US010556867B2

(12) United States Patent
Pazenok et al.

(10) Patent No.: US 10,556,867 B2
(45) Date of Patent: Feb. 11, 2020

(54) PROCESS FOR PREPARING 3-FLUOROALKYL-5-PYRAZOLECARBOXYLATES AND 3-FLUOROALKYL-5-PYRAZOLECARBOXYLIC ACIDS

(71) Applicants: BAYER CROPSCIENCE AKTIENGESELLSCHAFT, Monheim am Rhein (DE); CENTRE NATIONAL DE LA RECHERCHE SCIENTIFIQUE (CNRS), Paris (FR)

(72) Inventors: Sergii Pazenok, Solingen (DE); Jean-Pierre Vors, Sete (FR); Frédéric R. LeRoux, Herrlisheim (FR); Etienne Schmitt, Strasbourg (FR)

(73) Assignees: BAYER CROPSCIENCE AKTIENGESELLSCHAFT, Monheim am Rhein (DE); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 16/335,138

(22) PCT Filed: Sep. 18, 2017

(86) PCT No.: PCT/EP2017/073401
§ 371 (c)(1),
(2) Date: Mar. 20, 2019

(87) PCT Pub. No.: WO2018/054807
PCT Pub. Date: Mar. 29, 2018

(65) Prior Publication Data
US 2019/0225586 A1    Jul. 25, 2019

(30) Foreign Application Priority Data
Sep. 21, 2016   (EP) .................... 16290179

(51) Int. Cl.
*C07D 231/14*   (2006.01)
*C07C 251/08*   (2006.01)
*C07C 249/02*   (2006.01)
*C07D 401/04*   (2006.01)

(52) U.S. Cl.
CPC .......... *C07D 231/14* (2013.01); *C07C 249/02* (2013.01); *C07C 251/08* (2013.01); *C07D 401/04* (2013.01)

(58) Field of Classification Search
CPC .. C07D 231/14; C07D 401/04; C07C 249/02; C07C 251/08
USPC ...................................... 548/374.1
See application file for complete search history.

(56) References Cited

U.S. PATENT DOCUMENTS

| | | | |
|---|---|---|---|
| 7,329,633 | B2 | 2/2008 | Dunkel |
| 7,358,387 | B2 | 4/2008 | Lantzsch |
| 7,939,673 | B2 | 5/2011 | Pazenok |
| 8,629,288 | B2 | 1/2014 | Pazenok |

FOREIGN PATENT DOCUMENTS

| | | |
|---|---|---|
| WO | WO03000659 A1 | 1/2003 |
| WO | WO03/016282 A2 | 2/2003 |
| WO | WO03070705 A1 | 8/2003 |
| WO | WO2005042468 A1 | 5/2005 |
| WO | WO2008/013925 A2 | 1/2008 |
| WO | WO2008/022777 A2 | 2/2008 |
| WO | WO2009/106230 A2 | 9/2009 |
| WO | WO2012025557 A1 | 3/2012 |
| WO | WO2015144578 A1 | 10/2015 |

OTHER PUBLICATIONS

Barten, J. et al. (2004) "Novel β-hydroxy-β-bis(trifluoromethyl) imines," Journal of Fluorine Chemistry vol. 25; pp. 1039-1049.
European Search Report dated Dec. 21, 2016 for European Application No. 16290179.7, filed Sep. 21, 2016, 8 pages.
International Search Report dated Oct. 23, 2017, for International Application No. PCT/EP2017/073401, filed Sep. 18, 2017, 4 pages.
Khidre, R. et al. (Jan. 2016) "Synthetic Routes to Pyrazole-3(5)-carboxylates," J. Heterocyclic Chem., 53; pp. 13-31.
Mertens, L. et al. (2016) "Fluoroalkyl-Substituted Diazomethanes and Their Application in a General Synthesis of Pyrazoles and Pyrazolines," Chem. Eur. J., 22, pp. 9542-9545.
Perrone, S. et al. (2013) "Synthesis and reactivity of trifluoromethyl substituted oxaziridines," Tetrahedron 69; pp. 3878-3884.

*Primary Examiner* — Kristin A Vajda
(74) *Attorney, Agent, or Firm* — Morrison & Foerster LLP

(57) ABSTRACT

The present invention relates to a novel process for preparing 3-fluoroalkyl-5-pyrazolecarboxylates from ketimines and oxalic acid derivatives which can be further transformed into 3-fluoroalkyl-5-pyrazolecarboxylic acids.

11 Claims, No Drawings

PROCESS FOR PREPARING 3-FLUOROALKYL-5-PYRAZOLECARBOXYLATES AND 3-FLUOROALKYL-5-PYRAZOLECARBOXYLIC ACIDS

CROSS REFERENCE TO RELATED APPLICATIONS

This application is a national stage application under 35 U.S.C. § 371 of International Application No. PCT/EP2017/073401, filed internationally on Sep. 18, 2017, which claims priority benefit of European Application No. 16290179.7, filed Sep. 21, 2016.

The present invention relates to a novel process for preparing 3-fluoroalkyl-5-pyrazolecarboxylates from ketimines and oxalic acid derivatives which can be further transformed into 3-fluoroalkyl-5-pyrazolecarboxylic acids.

Polyfluoroalkylpyrazolylcarboxylic acid derivatives are valuable precursors of active fungicidal ingredients (WO 2003/070705, WO 2008/013925, WO 2003/000659, WO 2012/025557).

Pyrazolecarboxylic acid derivatives are typically prepared by reacting acrylic acid derivatives having two leaving groups with hydrazines (WO 2009/112157 and WO 2009/106230). WO 2005/042468 discloses a process for preparing 2-dihaloacyl-3-aminoacrylic esters by reacting acid halides with dialkylaminoacrylic esters and subsequent cyclization thereof with alkyl hydrazines. WO 2008/022777 describes a process for preparing 3-dihalomethylpyrazole-4-carboxylic acid derivatives by reacting α,α-difluoroamines in the presence of Lewis acids with acrylic acid derivatives and subsequent reaction thereof with alkylhydrazines. 3-fluoroalkyl-5-pyrazolecarboxylates are hardly accessible.

In the light of the prior art described above, it is an object of the present invention to provide a process that does not have the aforementioned disadvantages and hence gives a route to 3-fluoroalkyl-5-pyrazolecarboxylates derivatives in high yields.

The object described above was achieved by a process for preparing 3-fluoroalkyl-5-pyrazolecarboxylates of the formula (I),

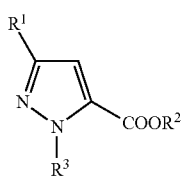
(I)

in which
$R^1$ is selected from $C_1$-$C_6$-haloalkyl;
$R^2$ is selected from $C_{1-12}$-alkyl, $C_{3-8}$-cycloalkyl, $C_{6-18}$-aryl and $C_{7-18}$-arylalkyl-,
$R^3$ is selected from H, $C_1$-$C_{12}$ alkyl, benzyl, phenyl, $C_{6-18}$-aryl and pyridyl;
characterized in that in step (A), oxalic acid derivatives of the formula (II),

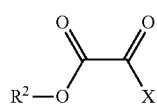
(II)

in which
$R^2$ is as defined above;
X is F, Cl or Br,
are reacted with compounds of the formula (III),

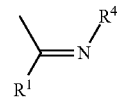
(III)

in which
$R^4$ is selected from $C_{1-12}$-alkyl, $C_{3-8}$-cycloalkyl, benzyl and $C_{7-18}$-arylalkyl-;
$R^1$ is as defined above;
in the presence of a base to form compounds of the formula (IV)

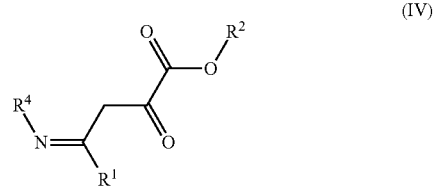
(IV)

in which
$R^1$, $R^2$, $R^4$ are as defined above
and that in step (B) in the presence of hydrazine $H_2N$—$NHR^3$ (V)
in which $R^3$ is as defined above
and an acid the cyclization of (IV) takes place to form (I).

Preferred is a process according to the invention, where the radicals of formula (I), (II), (III), (IV) and (V) are defined as follows:
$R^1$ is selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl ($CF_3CFH$), pentafluoroethyl and 1,1,1-trifluoroprop-2-yl;
$R^2$ is selected from methyl, ethyl, propyl and t-butyl, benzyl and phenylethyl-;
$R^3$ is selected from H, $C_1$-$C_8$ alkyl, aryl, benzyl and pyridyl;
$R^4$ is selected from methyl, ethyl, n-, iso-propyl, n-, iso-, secund t-butyl, cyclopropyl, cyclobutyl, cyclopentyl, cyclohexyl, phenyl, benzyl and phenylethyl-,
X is F or Cl.

More preferred is a process according to the invention, where the radicals in formula (I), (II), (III), (IV) and (V) are defined as follows:
$R^1$ is selected from trifluoromethyl, difluoromethyl, difluorochloromethyl and pentafluoroethyl;
$R^2$ is selected from methyl and ethyl;
$R^3$ is selected from H, methyl, ethyl, propyl, isopropyl, butyl, pentyl benzyl and phenyl;
$R^4$ is selected from benzyl and iso-propyl;
X is Cl;

Even more preferred is a process according to the invention, where the radicals in formula (I), (II), (III), (IV) and (V) are defined as follows:
$R^1$ is difluoromethyl, difluorochloromethyl or trifluoromethyl;

$R^2$ is methyl or ethyl;
$R^3$ is selected from H, methyl, ethyl, benzyl and phenyl;
$R^4$ is iso-propyl or benzyl;
X is Cl.

Most preferred is a process according to the invention, where the radicals in formula (I), (II), (III), (IV) and (V) are defined as follows:
$R^1$ is difluoromethyl or trifluoromethyl;
$R^2$ is methyl or ethyl;
$R^3$ is selected from H, methyl and phenyl;
$R^4$ is benzyl;
X is Cl.

Surprisingly, the pyrazoles of the formula (I) can be prepared under the inventive conditions with good yields and in high purity, which means that the process according to the invention overcomes the above mentioned disadvantages of the preparation processes previously described in the prior art.

A further aspect of the present invention are compounds of the formula (I)

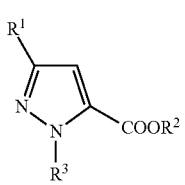

(I)

in which
$R^1$ is $CF_2H$;
$R^2$ is methyl or ethyl and
$R^3$ is methyl or phenyl.

A further aspect of the present invention are compounds of the formula (IV)

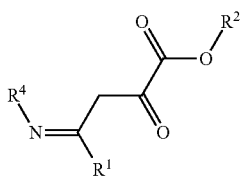

(IV)

in which
$R^1$ is difluoromethyl or trifluoromethyl;
$R^2$ is methyl or ethyl;
$R^4$ is iso-propyl or benzyl.

General Definitions

Haloalkyl: straight-chain or branched alkyl groups having 1 to 6 and preferably 1 to 3 carbon atoms, where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

Alkyl groups in the context of the present invention, unless defined differently, are linear or branched saturated hydrocarbyl groups. The definition $C_1$-$C_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl groups in the context of the present invention are aromatic hydrocarbons. The definition $C_{6-18}$-aryl encompasses the widest range defined herein for an aryl group having 6 to 18 carbon skeleton atoms. The definition encompasses, for example, phenyl, naphthyl and anthracenyl.

Arylalkyl-groups (aralkyl groups) in the context of the present invention are alkyl groups which are substituted by aryl groups. The definition $C_{7-18}$aralkyl group encompasses the widest range defined herein for an arylalkyl group having a total of 7 to 18 carbon atoms in the aromatic skeleton and the alkylene chain. This definition encompasses, for example, the meanings of benzyl and phenylethyl.

Process Description

The process is illustrated in Scheme 1:

Scheme 1:
Step (A)

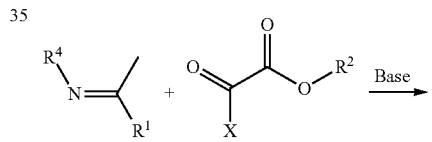

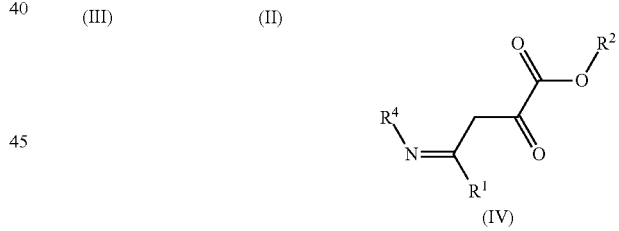

Step (B)

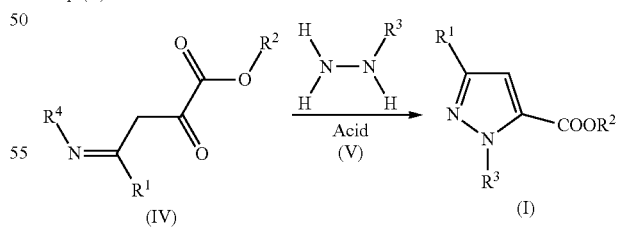

Step (A)

In step (A), oxalic acid derivatives of the formula (II) are reacted in the presence of a base with ketimines of the formula (III).

Preferred compounds of the formula (II) are methyloxalylchloride and ethyloxalylchloride.

Compounds of the formula (III) can be prepared from ketones according to literature methods: e.g. Roeschenthaler et al, J. Fluorine. Chem. v. 125, n. 6, 1039-1049; Tetrahedron, 69 (2013), 3878-3884 and WO 2015/144578.

For the process according to the invention 1 to 2 mol, preferably 1 to 1.5 mol, more preferably 1 to 1.2 mol of compound of the formula (II) is reacted with 1 mol of compound of the formula (III). The reaction time is not critical and may, according to the batch size and temperature, be selected within a range between a few minutes and several hours.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Preference is given to THF, acetonitriles, ethers, toluene, xylene, chlorobenzene, n-hexane, cyclohexane or methylcyclohexane, and particular preference to acetonitrile, THF, ether or dichloromethane.

The reaction of compound (III) and (II) according to the invention is effected at temperatures of −5° C. to +40° C., preferably at temperatures of +2° C. to +20° C., more preferably at 5° C. to +10° C. and under standard pressure.

Reaction is proceeded in the presence of a base. For the process according to the invention 1 to 2 mol, preferred 1.5 to 1.8 mol of the base for 1 mol compound of the formula (II) is used.

Suitable bases are trialkylamines (e.g. triethylamines), Hünig base, pyridines, alkylpyridines (e.g. methylpyridines). Preferred are pyridine, 3-methylpyridine, ethyldiisopropylamine.

The intermediates of the formula (IV) formed can be used in the cyclization step without prior workup. Alternatively, the intermediates can be isolated by suitable workup steps, characterized and optionally further purified.

Step (B)

According to the invention, 1 mol to 2 mol, preferably 1 to 1.5 mol of the hydrazine of the formula (V) $NH_2$—$NHR^3$ for 1 mol of the compound of formula (IV) is used.

The cyclization in step (B) of the compound of formula (IV) is effected at temperatures of −20° C. to +50° C., preferably at temperatures of +0° C. to +40° C., more preferably at +20° C. and under standard pressure.

The reaction time is not critical and may, according to the batch size, be selected within a relatively wide range.

Typically, the cyclization step (B) is effected without changing the solvent.

The cyclization of compound of the formula (IV) proceeds under acidic condition.

Suitable mineral acids are for example $H_2SO_4$, HCl, HF, HBr, HI, $H_3PO_4$ or organic acids, for example $CH_3COOH$, $CF_3COOH$, p-toluenesulphonic acid, methanesulphonic acid, trifluoromethanesulphonic acid.

According to the invention, 0.1 mol to 2 mol, preferably 0.1 to 1.5 mol of the acid for 1 mol of the compound of formula (IV) is used.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Preference is given to acetonitrile, ethanol, toluene, xylene, chlorobenzene, n-hexane, cyclohexane or methylcyclohexane, and particular preference to acetonitrile ethanol, THF, toluene or xylene. After the reaction has ended, for example, the solvents are removed and the product is isolated by filtration, or the product is first washed with water and extracted, the organic phase is removed and the solvent is removed under reduced pressure.

The compounds of the formula (I) can be converted into pyrazolecarboxylic acids of the formula (VI) by hydrolysis (Scheme 2).

Scheme 2:

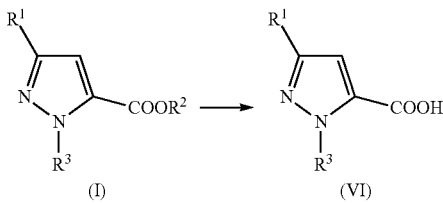

A further aspect of the present invention is therefore a process for preparing 3-fluoroalkyl-5-pyrazole acids (VI),

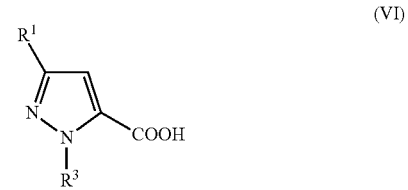

in which
$R^1$ is selected from $C_1$-$C_6$-haloalkyl; and
$R^3$ is selected from H, $C_1$-$C_{12}$ alkyl, benzyl, phenyl, $C_{6-18}$-aryl and pyridyl;
comprising
(i) the process for preparing 3-fluoroalkyl-5-pyrazolecarboxylates of the formula (I), in particular 3-fluoroalkyl-5-pyrazolecarboxylates of the formula (I) where $R^2$ equals $C_{1-12}$-alkyl, and
(ii) hydrolysing the compounds of the formula (I) to the compound of the formula (VI).

The hydrolysis can be performed under acidic or basic conditions. The reaction can likewise be performed without addition of acid, only in water.

For acidic hydrolysis, preference is given to the following mineral acids: $H_2SO_4$, HCl, $HSO_3Cl$, HF, HBr, HI, $H_3PO_4$ or the following organic acids: $CF_3COOH$, p-toluenesulphonic acid, methanesulphonic acid, trifluoromethanesulphonic acid. The reaction can be accelerated by the addition of catalysts, for example $FeCl_3$, $AlCl_3$, $BF_3$, $SbCl_3$, $NaH_2PO_4$.

Basic hydrolysis is effected in the presence of inorganic bases such as alkali metal hydroxides, for example lithium hydroxide, sodium hydroxide or potassium hydroxide, alkali metal carbonates, for example $Na_2CO_3$, $K_2CO_3$ and alkali metal acetates, for example NaOAc, KOAc, LiOAc, and alkali metal alkoxides, for example NaOMe, NaOEt, NaOt-Bu, KOt-Bu of organic bases such as trialkylamines, alkylpyridines, phosphazenes and 1,8-diazabicyclo[5.4.0]undecene (DBU). Preference is given to the inorganic bases, for example NaOH, KOH, $Na_2CO_3$ or $K_2CO_3$.

Preference is given to conversion by means of basic hydrolysis.

The process step of the invention is performed within a temperature range from 20° C. to +150° C., preferably at temperatures of 30° C. to +110° C., more preferably at 30° C. to 80° C.

The process step of the invention is generally performed under standard pressure. Alternatively, however, it is also possible to work under vacuum or under elevated pressure (for example reaction in an autoclave with aqueous HCl).

The reaction time may, according to the batch size and the temperature, be selected within a range between 1 hour and several hours.

The reaction step can be performed in substance or in a solvent. Preference is given to performing the reaction in a solvent. Suitable solvents are, for example, selected from the group comprising water, alcohols such as methanol, ethanol, isopropanol or butanol, aliphatic and aromatic hydrocarbons, for example n-hexane, benzene or toluene, which may be substituted by fluorine and chlorine atoms, such as methylene chloride, dichloroethane, chlorobenzene or dichlorobenzene; ethers, for example diethyl ether, diphenyl ether, methyl tert-butyl ether, isopropyl ethyl ether, dioxane, diglyme, dimethylglycol, dimethoxyethane (DME) or THF; nitriles such as methyl nitrile, butyl nitrile or phenyl nitrile; amides we dimethylformamide (DMF) or N-methylpyrrolidone (NMP) or mixtures of such solvents, particular preference being given to water, acetonitrile, dichloromethane and alcohols (ethanol).

A further aspect of the present invention are compounds of the formula (VI)

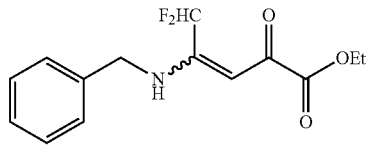

(VI)

in which
$R^1$ is $CF_2H$;
$R^3$ is methyl, ethyl or phenyl.

EXPERIMENTAL PART

Example 1

N-(1,1-difluoropropan-2-ylidene)propan-2-amine, (III-1)

To the mixture of difluoracetone (94 g, 1 mol) in 500 ml methylt-butylether 88 g (1.5 mol) of isopropylamin was added at 10° C. After 1 h 70 g (0.5 mol) $BF_3*Et_2O$ was added and the mixture was stirred additionally for 1 h. The organic solution was separated from bottom syrup and the solvent was distilled off at atmospheric pressure. The remaining liquid was distilled in vacuum yielding 139 g ketimine with a b.p. of 70-72° C./400 mbar.

$^1$H NMR (400 MHz, $CDCl_3$): δ 5,9 (t, 1H), 3,7 (m, 1H), 1,8 (s, 3H), 1,1 (d, 6H) ppm.
$^{19}$F (376 MHz, $CDCl_3$) δ –122 (d, 2F) ppm.

Example 2

N-1,1-difluoropropan-2-ylidene-1-phenylmethanamine, (III-2)

To the mixture of difluoroacetone (94 g, 1 mol) in 500 ml dichloromethane 107 g (1 mol) of benzylamine was slowly added at 10° C. After 6 h at 20° C., $CH_2Cl_2$ was distilled off at reduced pressure and the remaining liquid was distilled in vacuum, yielding 161 g ketimine with b.p. 80-82° C./1.3 mbar.

$^1$H NMR (400 MHz, $CDCl_3$) δ 7,2-7,4 (m, 5H), 5,9 (t, 1H), 4,5 (s, 2H), 2,0 (s, 3H) ppm.
$^{19}$F (376 MHz, $CDCl_3$) δ –1118 (d, 2F) ppm.

Example 3

Ethyl 4-(benzylamino)-5,5-difluoro-2-oxopent-3-enoate (IV-1)

A solution of benzyl(1,1-difluoropropan-2-ylidene)amine (1 eq., 250 mg, 1.30 mmol) in dichloromethane (2 mL) was cooled to –20° C. Pyridine (1.05 eq., 108 mg, 0.11 mL, 1.36 mmol) was added, followed by a solution of ethyl oxalyl monochloride (1.03 eq., 183 mg, 0.15 mL, 1.34 mmol) in dichloromethane (1 mL). The mixture was stirred from –20° C. to room temperature over 18 h.

The mixture was taken up in dichloromethane (5 mL) followed by $Et_2O$ (10 mL). The resulting precipitate was filtered off, the filtrate concentrated in vacuo. The crude product was purified by flash chromatography (AcOEt in cyclohexane 0 to 15%) to yield 4-(benzylamino)-5,5-difluoro-2-oxopent-3-enoate (224 mg, 0.79 mmol, 61%) as an orange oil.

NMR $^1$H ($CDCl_3$, 400 MHz): 10.91 (s br, NH), 7.39 to 7.28 (m, 5H, Phenyl), 6.18 (t, $CHF_2$, J=53 Hz), 6.17 (s, CHCO), 4.66 (d, $CH_2NH$), 4.31 (q, $OCH_2$), 1.36 (t, $OCH_2CH_3$) ppm.

NMR $^{19}$F ($CDCl_3$, 376 MHz): –118.9 (d, $CHF_2$, J=53 Hz) ppm.

NMR $^{13}$C ($CDCl_3$, 100 MHz): 180.2 (C(O)COOEt), 162.6 (C(O)OEt), 156.8 (t, $CCHF_2$, J=22 Hz), 1362, 1292, 128.3, 127.3 ($C_{Phenyl}$), 111.4 (t, $CHF_2$, J=245 Hz), 91.4 (t, CHCO, J=7 Hz), 62.2 ($OCH_2$), 48.2 ($CH_2NH$), 14.1 ($OCH_2CH_3$) ppm.

Anal. calcd for $C_{14}H_{15}F_2NO_3$: C, 59.36; H, 5.34; F, 13.41; N, 4.94; 0, 16.94. Found: C, 59.16; H, 5.36; N, 4.95.

Example 4

Methyl 4-(benzylamino)-5,5,5-trifluoro-2-oxopent-3-enoate (IV-2)

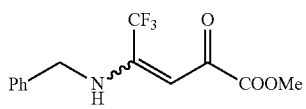 [SMILES: COC(=O)C(=O)C=C(NCc1ccccc1)C(F)(F)F]

A solution of benzyl(1,1,1-trifluoropropan-2-ylidene)amine (1 eq., 1000 mg, 4.82 mmol) in dichloromethane (10 mL) was cooled to −20° C. Pyridine (1.03 eq., 391 mg, 0.4 mL, 4.95 mmol) was added, followed by a solution of methyl oxalyl chloride (1.06 eq., 625 mg, 0.47 mL, 5.1 mmol) in dichloromethane (6 mL). The mixture was stirred from −20° C. to room temperature over 18 h and was then concentrated and purified by flash chromatography (AcOEt in cyclohexane 0 to 10%), to yield methyl 4-(benzylamino)-5,5,5-trifluoro-2-oxopent-3-enoate (680 mg, 2.37 mmol, 49%) as a colourless oil.

NMR $^1$H (CDCl$_3$, 400 MHz): 11.02 (s br, NH), 7.40 to 7.28 (m, 5H, Phenyl), 6.40 (s, CHCO), 4.64 (d, CH$_2$NH), 3.87 (s, COOCH$_3$) ppm.

NMR $^{19}$F (CDCl$_3$, 376 MHz): −66.6 (s, CF$_3$) ppm.

NMR $^{13}$C (CDCl$_3$, 100 MHz): 1803 (CHCO), 162.7 (COOMe), 152.6 (q, CCF$_3$, J=32.5 Hz), 135.8, 129.3, 128.5, 127.4 (C$_{Phenyl}$), 119.6 (q, CF$_3$, J=278 Hz), 90.4 (q, CHCO, J 5 Hz), 53.1 (COOCH$_3$), 49.0 (CH$_2$NH) ppm.

HRMS (ESI) calcd for C$_{13}$H$_{12}$F$_3$NNaO$_3$ [M+Na]: 310.0661. Found: 310.0635.

Example 5

Ethyl 3-(difluoromethyl)-1-methyl-1H-pyrazole-5-carboxylate (I-1)

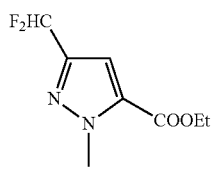

A solution of ethyl 4-(benzylamino)-5,5-difluoro-2-oxopent-3-enoate (1 eq., 520 mg, 1.78 mmol) in MeCN (4 mL) was treated with methyl hydrazine (1.57 eq., 129 mg, 0.15 mL, 2.8 mmol) followed by concentrated H$_2$SO$_4$ (0.511 eq., 92 mg, 0.05 mL, 0.91 mmol) under inert atmosphere at room temperature.

The mixture was stirred 1 h and then was diluted with dichloromethane, filtered and concentrated in vacuo. The crude product was purified by flash chromatography (Et$_2$O in pentane 0 to 40%), to yield ethyl 3-(difluoromethyl)-1-methyl-1H-pyrazole-5-carboxylate as a colourless oil (230 mg, 63%).

NMR $^1$H (CDCl3, 400 MHz): 7.04 (t, 4-CH, J=1 Hz), 6.66 (t, CHF$_2$, J=55 Hz), 4.36 (q, OCH$_2$), 4.19 (s, CH$_3$), 1.38 (t, OCH$_2$CH$_3$) ppm.

NMR $^{19}$F (CDCl$_3$, 376 MHz): −112.1 (d, CHF$_2$, J=55 Hz) ppm.

NMR $^{13}$C (CDCl3, 100 MHz): 159.4 (C=O), 145.1 (t, CCHF$_2$, J=29.8 Hz), 134.0 (CCOOEt), 110.8 (t, CHF$_2$, J=234 Hz), 108.7 (4-CH), 61.5 (OCH$_2$), 40.1 (NCH$_3$), 14.3 (OCH$_2$CH$_3$) ppm.

HRMS (ESI) calcd for C$_8$H$_{11}$F$_2$N$_2$O$_2$ [M+H]: 205.0783. Found: 205.0782.

Example 6

3-(difluoromethyl)-1-methyl-1H-pyrazole-5-carboxylic acid (VI-1)

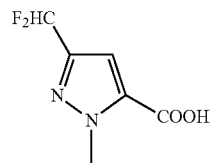

A mixture of ethyl 3-(difluoromethyl)-1-methyl-1H-pyrazole-5-carboxylate (1 eq., 185 mg, 0.906 mmol) and 2N NaOH (2.01 eq., 2 M, 0.912 mL, 1.82 mmol) in EtOH (2.61 mL) was stirred at room temperature for 1 h. The mixture was treated with HCl 1N until pH 2-3, then was extracted with dichloromethane. The combined organic layer was washed with brine and dried over (Na$_2$SO$_4$), filtered and evaporated in vacuo, to yield a white solid (160 mg, 99%) after trituration in pentane.

M.p.: 179.8 to 180.2° C.

NMR $^1$H (d$^6$-DMSO, 400 MHz): 13.7 (s br, COOH), 7.02 (s, 4-CH), 7.01 (t, CHF$_2$, J=54.4 Hz), 4.11 (s, NCH$_3$) ppm.

NMR $^{19}$F (d$^6$-DMSO, 376 MHz): −111.6 (d, CHF$_2$, J=54.5 Hz) ppm.

NMR $^{13}$C (d$^6$-DMSO, 100 MHz): 160.1 (C=O), 144.0 (t, CCHF$_2$, J=28.5 Hz), 134.6 (CCOOH), 110.9 (t, CHF$_2$, J=232 Hz), 108.4 (4-CH), 39.7 (NCH$_3$) ppm.

Example 7

Ethyl 3-(difluoromethyl)-1-phenyl-1H-pyrazole-5-carboxylate (I-2)

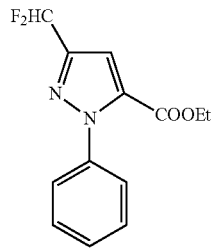

A solution of ethyl 4-(benzylamino)-5,5-difluoro-2-oxopent-3-enoate (1 eq., 420 mg, 1.44 mmol) in MeCN (4 mL) was treated with phenyl hydrazine (1.47 eq., 228 mg, 0.21 mL, 2.12 mmol) followed by concentrated H$_2$SO$_4$ (0.506 eq., 73.6 mg, 0.04 mL, 0.728 mmol) under inert atmosphere. The mixture was refluxed overnight. Dichloromethane (20 mL) was added, the mixture filtered and concentrated in vacuo. The crude product was purified by flash chromatography (AcOEt in cyclohexane 0 to 2%), to give 310 mg of orange oil.

NMR $^1$H (CDCl3, 400 MHz): 7.50 to 7.41 (m, 5H, $C_{Phenyl}$), 7.24 (s, 4-CH), 6.76 (t, $CHF_2$, J=54.9 Hz), 4.26 (q, $OCH_2$), 1.26 (t, $OCH_2CH_3$) ppm.

NMR $^{19}$F (CDCl3, 376 MHz): −112.2 (d, $CHF_2$, J=54.6 Hz) ppm.

NMR $^{13}$C (CDCl3, 100 MHz): 158.4 (C=O), 146.8 (t, $CCHF_2$, J=30 Hz), 139.8 ($NC_{Phenyl}$), 135.0 (CCOOEt), 1292, 128.7, 126.0 ($C_{Phenyl}$), 110.7 (t, $CHF_2$, J=234 Hz), 109.6 (4-CH), 61.6 ($OCH_2$), 13.9 ($OCH_2CH_3$) ppm.

HRMS (ESI) calcd for $C_{13}H_{13}F_2N_2O_2$ [M+H]: 267.0940. Found: 267.0918.

Example 8

3-(Difluoromethyl)-1-phenyl-1H-pyrazole-5-carboxylic acid (VI-2)

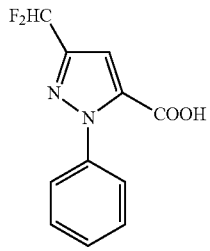 [SMILES: CCOC(=O)c1cc(C(F)F)nn1-c1ccccc1]

A mixture of ethyl 3-(difluoromethyl)-1-phenyl-1H-pyrazole-5-carboxylate (1 eq., 160 mg, 0.601 mmol) and 2N NaOH (1.83 eq., 2 M, 0.55 mL, 1.1 mmol) in EtOH (1 mL) was stirred at room temperature for 1 h. The mixture was acidified with HCl 1N to pH 2-3, then was extracted with dichloromethane. The combined organic layer was washed (brine), dried ($Na_2SO_4$), filtered and evaporated in vacuo, to yield a brown solid (160 mg) after trituration in pentane. M.p.: 132.7 to 133.5° C.

NMR $^1$H ($d^6$-DMSO, 400 MHz): 13.6 (COOH), 7.50 (m, 5H, $C_{Phenyl}$), 7.25 (s, 4-CH), 7.13 (t, $CHF_2$, J=54 Hz) ppm.

NMR $^{19}$F ($d^6$-DMSO, 376 MHz): −1122 (d, $CHF_2$, J=53.7 Hz) ppm.

NMR $^{13}$C ($d^6$-DMSO, 100 MHz): 159.3 (COOH), 146.0 (t, $CCHF_2$, J=29 Hz), 139.7 ($NC_{Phenyl}$), 135.9 (CCOOH), 128.9, 128.7, 125.9 ($C_{Phenyl}$), 110.9 (t, $CHF_2$, J=233 Hz), 109.5 (4-CH) ppm.

Anal. calcd for $C_{11}H_8F_2N_2O_2$: C, 55.47; H, 3.39; F, 15.95; N, 11.76; O, 13.43. Found: C, 55.97; H, 3.54; N, 11.61.

Example 9

Methyl 1-methyl-3-(trifluoromethyl)-1H-pyrazole-5-carboxylate (I-3)

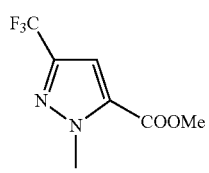

A solution of methyl 4-(benzylamino)-5,5,5-trifluoro-2-oxopent-3-enoate (1 eq., 150 mg, 0.47 mmol) in MeCN (1 mL) was treated with methyl hydrazine (1.59 eq., 34.4 mg, 40 µL, 0.747 mmol) followed by concentrated $H_2SO_4$ (0.503 eq., 23.9 mg, 13 µL, 0237 mmol) under inert atmosphere at room temperature. The mixture was stirred at 90° C. for 1 h and removed from oil bath for 5 min. Pyridine (8.02 eq., 298 mg, 305 µL, 3.77 mmol) was added, followed by $SOCl_2$ (2.05 eq., 114 mg, 70 µL, 0.965 mmol). The mixture was stirred 30 min. Internal standard: fluorobenzene (1.13 eq., 51 mg, 50 µL, 0.531 mmol). $^{19}$F NMR yield: >99%.

Example 10

Methyl 1-phenyl-3-(trifluoromethyl)-1H-pyrazole-5-carboxylate (I-4)

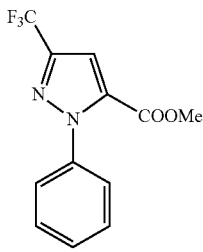 [SMILES: COC(=O)c1cc(C(F)(F)F)nn1-c1ccccc1]

A solution of methyl 4-(benzylamino)-5,5,5-trifluoro-2-oxopent-3-enoate (1 eq., 500 mg, 1.74 mmol) in MeCN (5 mL) was treated with phenylhydrazine (1.51 eq., 283 mg, 0.26 mL, 2.62 mmol) rapidly followed by concentrated $H_2SO_4$ (0.523 eq., 92 mg, 0.05 mL, 0.91 mmol) under inert atmosphere at room temperature. The mixture was refluxed for 2 days and cooled to room temperature. Pyridine (7.81 eq., 1075 mg, 1.1 mL, 13.6 mmol) was added, followed by a slow addition of $SOCl_2$ (1.98 eq., 410 mg, 0.25 mL, 3.45 mmol) via syringe. The mixture was stirred 30 min.

The mixture was filtered and concentrated in vacuo. The crude was purified by flash chromatography ($Et_2O$ in pentane 0 to 5%), to give 370 mg of solid (ca. 80 wt. %=300 mg, 64%).

HRMS (ESI) calcd for $C_{12}H_{10}F_3N_2O_2$ [M+H]: 271.0689. Found: 271.0697.

Example 11

1-phenyl-3-(trifluoromethyl)-1H-pyrazole-5-carboxylic acid (VI-3)

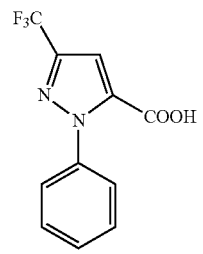 [SMILES: O=C(O)c1cc(C(F)(F)F)nn1-c1ccccc1]

A mixture of methyl 1-phenyl-3-(trifluoromethyl)-1H-pyrazole-5-carboxylate (1 eq., 170 mg, 0.503 mmol) and 2N NaOH (2.19 eq., 2 M, 0.55 mL, 1.1 mmol) in EtOH (1 mL) was stirred at room temperature for 1 h. The mixture was treated with 1N HCl until pH 2-3, then was extracted with dichloromethane. The combined organic layer was washed (brine), dried (Na$_2$SO$_4$), filtered and evaporated in vacuo, to yield a brown solid. M.p.: 155-165° C. (degradation observed).

NMR $^1$H (d$^6$-DMSO, 400 MHz): 13.7 (s br, COOH), 7.52 (m, 5H, CH$_{Phenyl}$), 7.50 (4-CH) ppm.

NMR $^{19}$F (d$^6$-DMSO, 376 MHz): −60.9 (s, CF$_3$) ppm.

NMR $^{13}$C (d$^6$-DMSO, 100 MHz): 158.9 (COOH), 141.0 (q, CCF$_3$, J=38 Hz), 139.4 (N-1 C$_{Phenyl}$), 136.4 (CCOOH), 129.3, 128.7, 126.0 (2-6 C$_{Phenyl}$), 120.9 (q, CF$_3$, J=269 Hz), 110.1 (4-CH) ppm.

HRMS (ESI) calcd for C$_{11}$H$_8$F$_3$N$_2$O$_2$ [M+H]: 257.0532. Found: 257.0536.

The invention claimed is:

1. A process for preparing a 3-fluoroalkyl-5-pyrazolecarboxylate of formula (I),

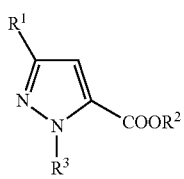

(I)

in which

R$^1$ is C$_1$-C$_6$-haloalkyl;

R$^2$ is selected from the group consisting of C$_{1-12}$-alkyl, C$_{3-8}$-cycloalkyl, C$_{6-18}$-aryl, and C$_{7-18}$-arylalkyl-;

R$^3$ is selected from the group consisting of H, C$_1$-C$_{12}$ alkyl, benzyl, phenyl, C$_{6-18}$-aryl, and pyridyl;

the process comprising:

in step (A), reacting an oxalic acid derivative of formula (II),

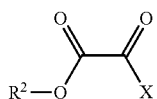

(II)

in which

R$^2$ is as defined above;

X is F, Cl or Br;

with a compound of formula (III),

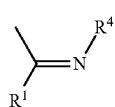

(III)

in which

R$^4$ is selected from the group consisting of C$_{1-12}$-alkyl, C$_{3-8}$-cycloalkyl, benzyl, and C$_{7-18}$-arylalkyl-;

R$^1$ is as defined above;

in the presence of a base to form a compound of formula (IV)

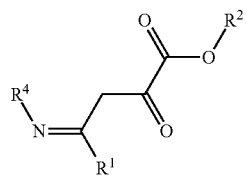

(IV)

in which

R$^1$, R$^2$, R$^4$ are as defined above; and in step (B), reacting the compound of formula (IV) with a hydrazine of formula H$_2$N—NHR$^3$ (III)

in which R$^3$ is as defined above;

and an acid to form the 3-fluoroalkyl-5-pyrazolecarboxylate of formula (I).

2. The process according to claim 1, wherein:

R$^1$ is selected from the group consisting of difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl (CF$_3$CFH), pentafluoroethyl, and 1,1,1-trifluoroprop-2-yl;

R$^2$ is selected from the group consisting of methyl, ethyl, propyl and t-butyl, benzyl, and phenylethyl-;

R$^3$ is selected from the group consisting of H, C$_1$-C$_8$ alkyl, aryl, benzyl and pyridyl;

R$^4$ is selected from the group consisting of methyl, ethyl, n-, iso-propyl, n-, iso-, sec-und t-butyl, cyclopropyl, cyclobutyl, cyclopentyl, cyclohexyl, phenyl, benzyl, and phenylethyl-; and X is F or Cl.

3. The process according to claim 1, wherein:

R$^1$ is selected from the group consisting of trifluoromethyl, difluoromethyl, difluorochloromethyl, and pentafluoroethyl;

R$^2$ is selected from the group consisting of methyl and ethyl;

R$^3$ is selected from the group consisting of H, methyl, ethyl, propyl, isopropyl, butyl, pentyl, benzyl, and phenyl;

R$^4$ is selected from the group consisting of benzyl and iso-propyl;

X is Cl.

4. The process according to claim 1, wherein:

R$^1$ is difluoromethyl, difluorochloromethyl or trifluoromethyl;

R$^2$ is methyl or ethyl;

R$^3$ is selected from the group consisting of H, methyl, ethyl, benzyl, and phenyl;

R$^4$ is iso-propyl or benzyl; and

X is Cl.

5. The process according to claim 1, wherein:

R$^1$ is difluoromethyl or trifluoromethyl;

R$^2$ is methyl or ethyl;

R$^3$ is selected from the group consisting of H, methyl, and phenyl;

R$^4$ is benzyl; and

X is Cl.

6. The process according to claim 1, wherein the base in step (A) is selected from the group consisting of pyridine, 3-methylpyridine, and ethyldiisopropylamine.

7. The process according to claim 1,
wherein the acid in step (B) is selected from the group consisting of $H_2SO_4$, HCl, HF, HBr, HI, $H_3PO_4$, $CH_3COOH$, $CF_3COOH$, p-toluenesulphonic acid, methanesulphonic acid, and trifluoromethanesulphonic acid.

8. A process for preparing a 3-fluoroalkyl-5-pyrazole acid, of formula (VI),

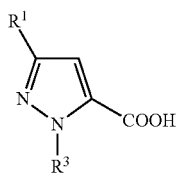

(VI)

in which
$R^1$ is $C_1$-$C_6$-haloalkyl;
$R^3$ is selected from the group consisting of H, $C_1$-$C_{12}$ alkyl, benzyl, phenyl, $C_{6-18}$-aryl, and pyridyl;
comprising
(i) the process according to claim 1, and
(ii) hydrolysing the compound of the formula (I) to form the compound of the formula (VI).

9. The process according to claim 8, wherein the hydrolysis reaction is performed under basic conditions.

10. A compound of formula (IV)

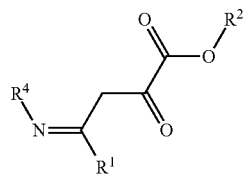

(IV)

in which
$R^1$ is difluoromethyl or trifluoromethyl;
$R^2$ is methyl or ethyl; and
$R^4$ is iso-propyl or benzyl.

11. The process according to claim 9, wherein the basic conditions comprise the
presence of a base selected from the group consisting of NaOH, KOH, $Na_2CO_3$, and $K_2CO_3$.

* * * * *